(12) United States Patent
Cho et al.

(10) Patent No.: US 8,410,294 B2
(45) Date of Patent: Apr. 2, 2013

(54) METHOD FOR PREPARING HIGHLY PURE ANHYDROUS CRYSTALLINE DOCETAXEL

(75) Inventors: Jin-Suk Cho, Daejeon (KR); Moon-Suk Kim, Daejeon (KR); Jai-Young Song, Daejeon (KR); Jeong-Hwan Yun, Daejeon (KR); Jong-Won Yoon, Yuseong-Ku (KR); Ho-Joon Choi, Gyeonggi-do (KR)

(73) Assignee: Samyang Genexbio Corporation, Seoul (KR)

( * ) Notice: Subject to any disclaimer, the term of this patent is extended or adjusted under 35 U.S.C. 154(b) by 0 days.

(21) Appl. No.: 13/518,630

(22) PCT Filed: Dec. 27, 2010

(86) PCT No.: PCT/KR2010/009344
§ 371 (c)(1),
(2), (4) Date: Jun. 22, 2012

(87) PCT Pub. No.: WO2011/081373
PCT Pub. Date: Jul. 7, 2011

(65) Prior Publication Data
US 2013/0046104 A1 Feb. 21, 2013

(30) Foreign Application Priority Data
Dec. 31, 2009 (KR) .................. 10-2009-0135668

(51) Int. Cl.
*C07D 305/14* (2006.01)
(52) U.S. Cl. ...................................................... 549/510
(58) Field of Classification Search .................. 549/510
See application file for complete search history.

(56) References Cited

U.S. PATENT DOCUMENTS

| | | |
|---|---|---|
| 5,688,977 A | 11/1997 | Sisti et al. |
| 6,838,569 B2 | 1/2005 | Sharma et al. |
| 2003/0225291 A1 | 12/2003 | Sharma et al. |
| 2008/0200700 A1 | 8/2008 | Gabetta et al. |

FOREIGN PATENT DOCUMENTS

WO WO-2007/078050 A2 7/2007

OTHER PUBLICATIONS

International Search Report dated Sep. 9, 2011 relating to PCT/KR2010/009344.
Notice of Allowance for KR Patent Application No. 10-2009-0135668 dated Apr. 30, 2012.

*Primary Examiner* — Kristin Bianchi
(74) *Attorney, Agent, or Firm* — Gifford, Krass, Sprinkle, Anderson & Citkowski, P.C.

(57) ABSTRACT

A method for preparing highly pure anhydrous crystalline docetaxel is provided. The method for preparing highly pure anhydrous crystalline docetaxel enables preparation of anhydrous crystalline docetaxel that has purity of 99.5% or more, and is useful as an anticancer agent due to remarkably low residual solvent content compared to the standard of residual solvents in drugs.

24 Claims, 11 Drawing Sheets

[Figure 1]
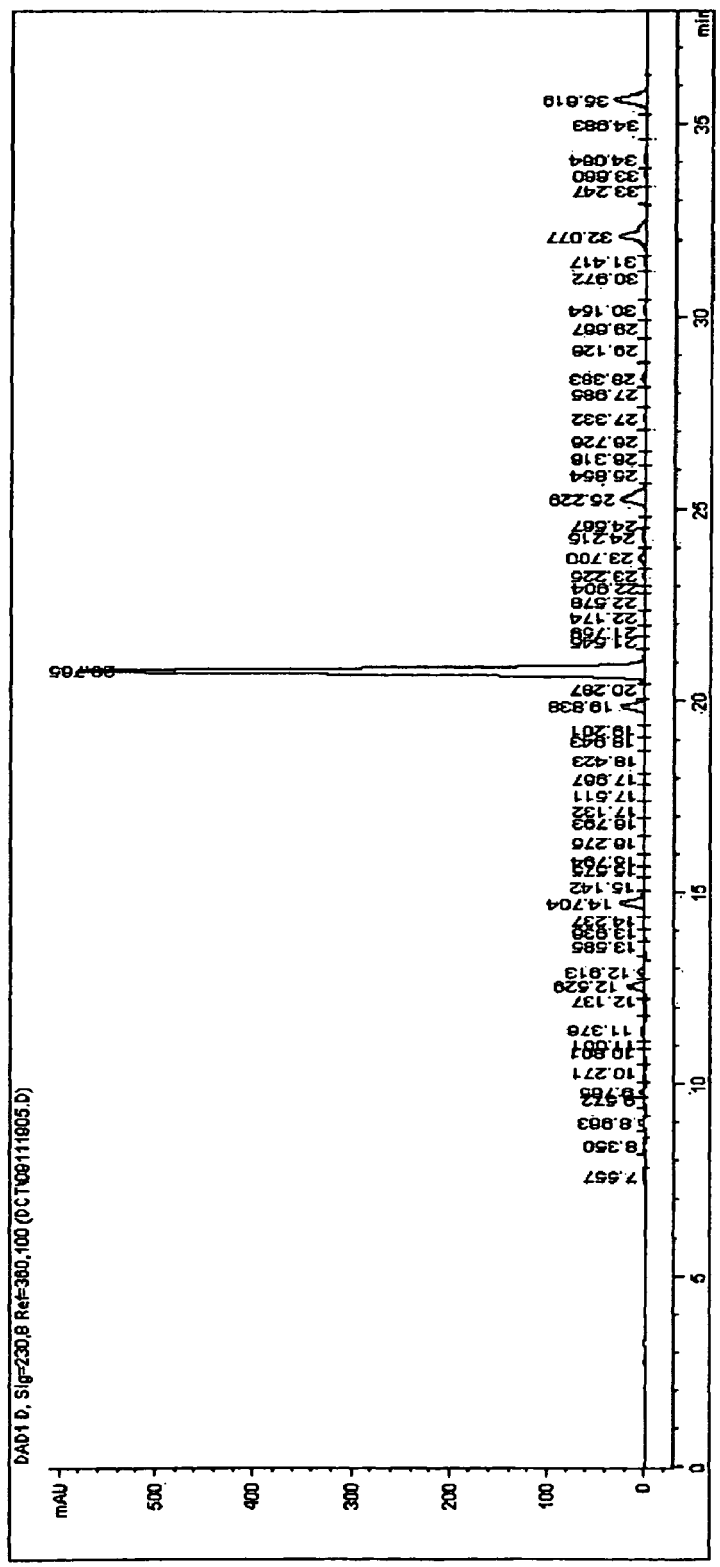

[Figure 2]
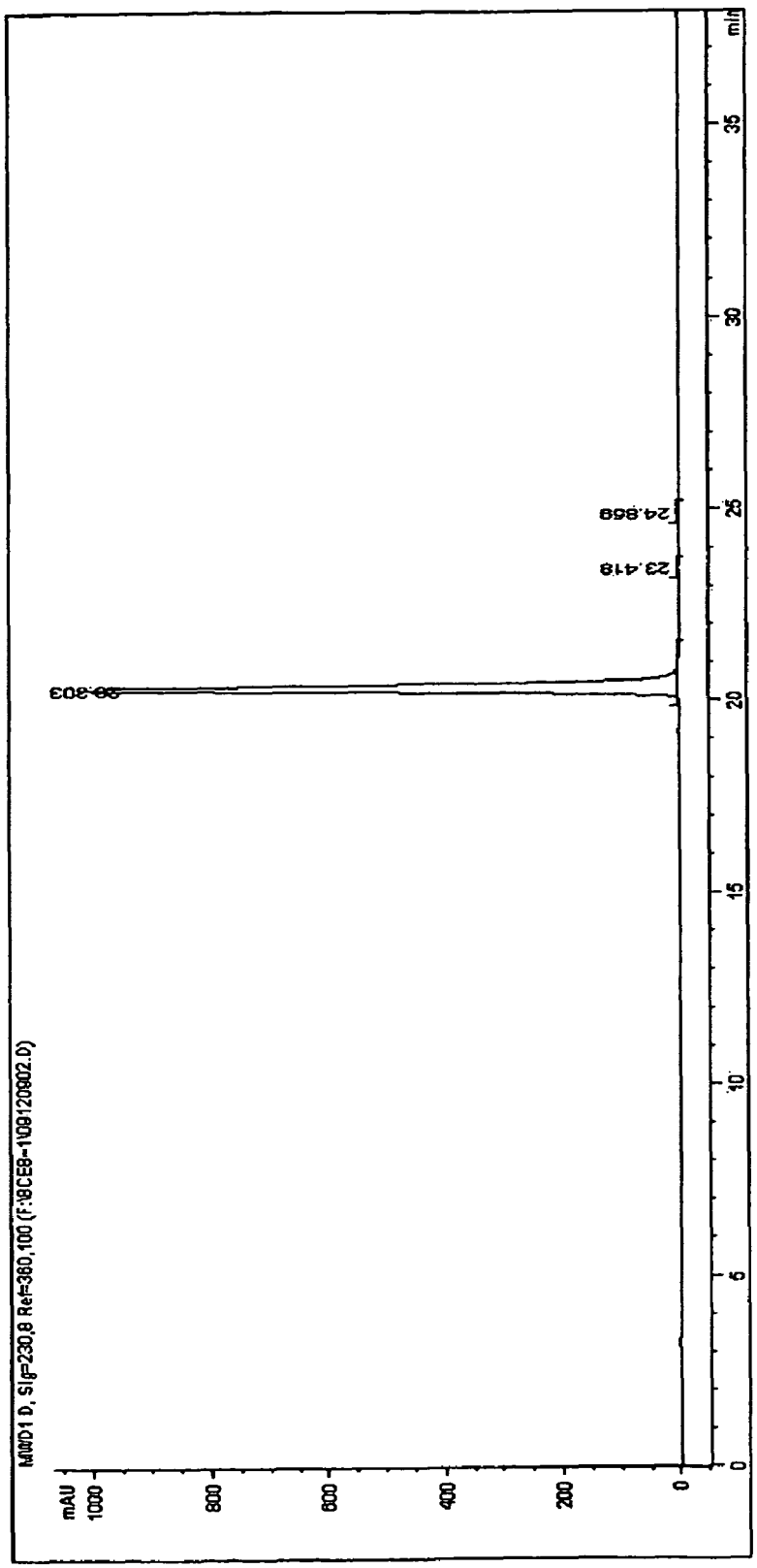

[Figure 3]
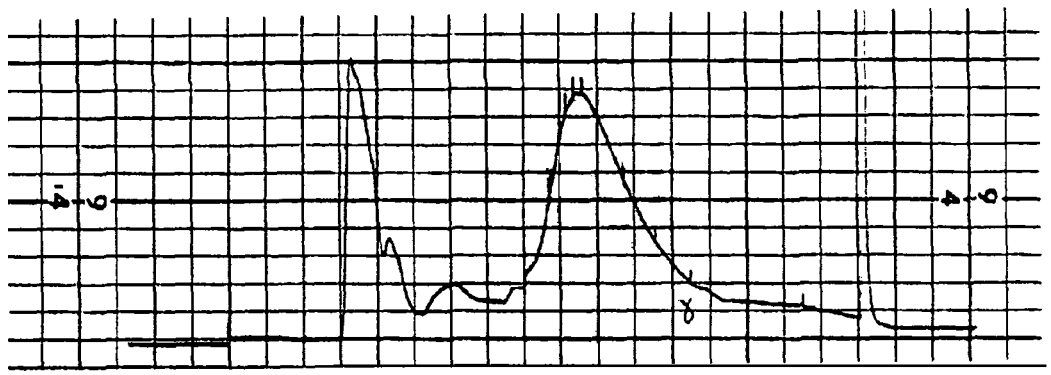
[Figure 4]
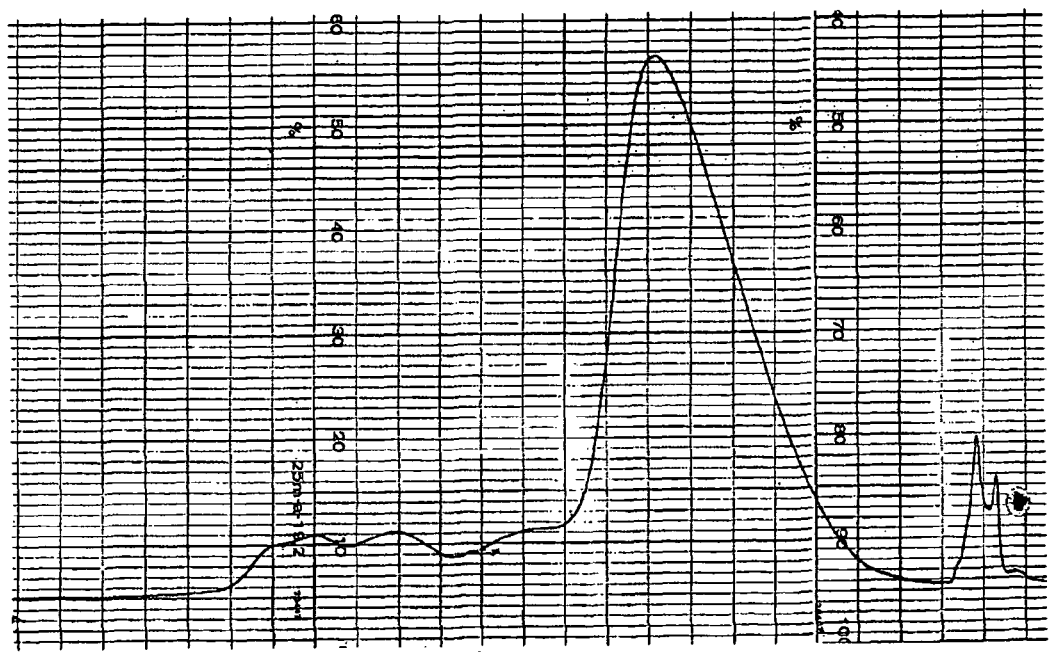

[Figure 5]
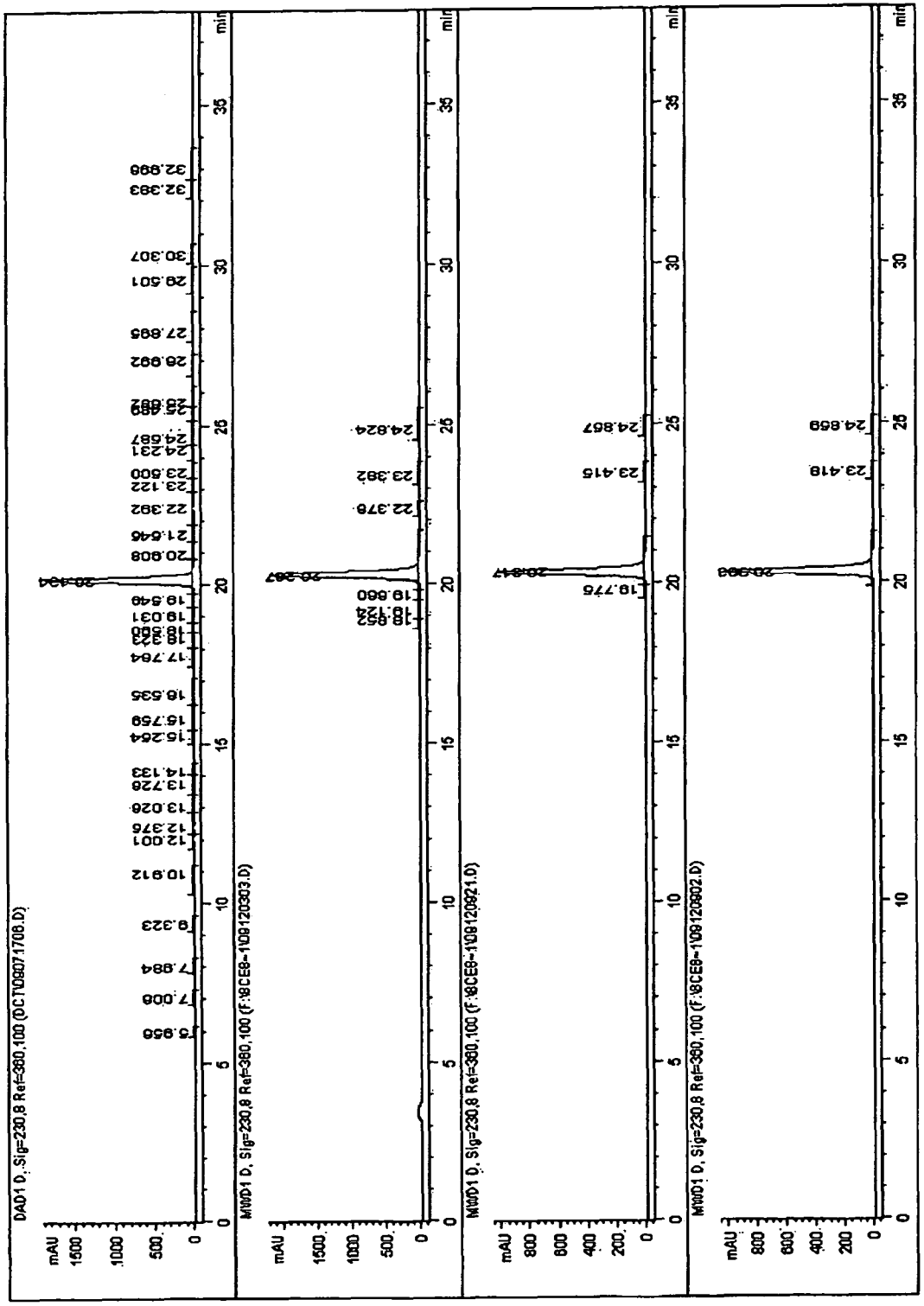

[Figure 6]
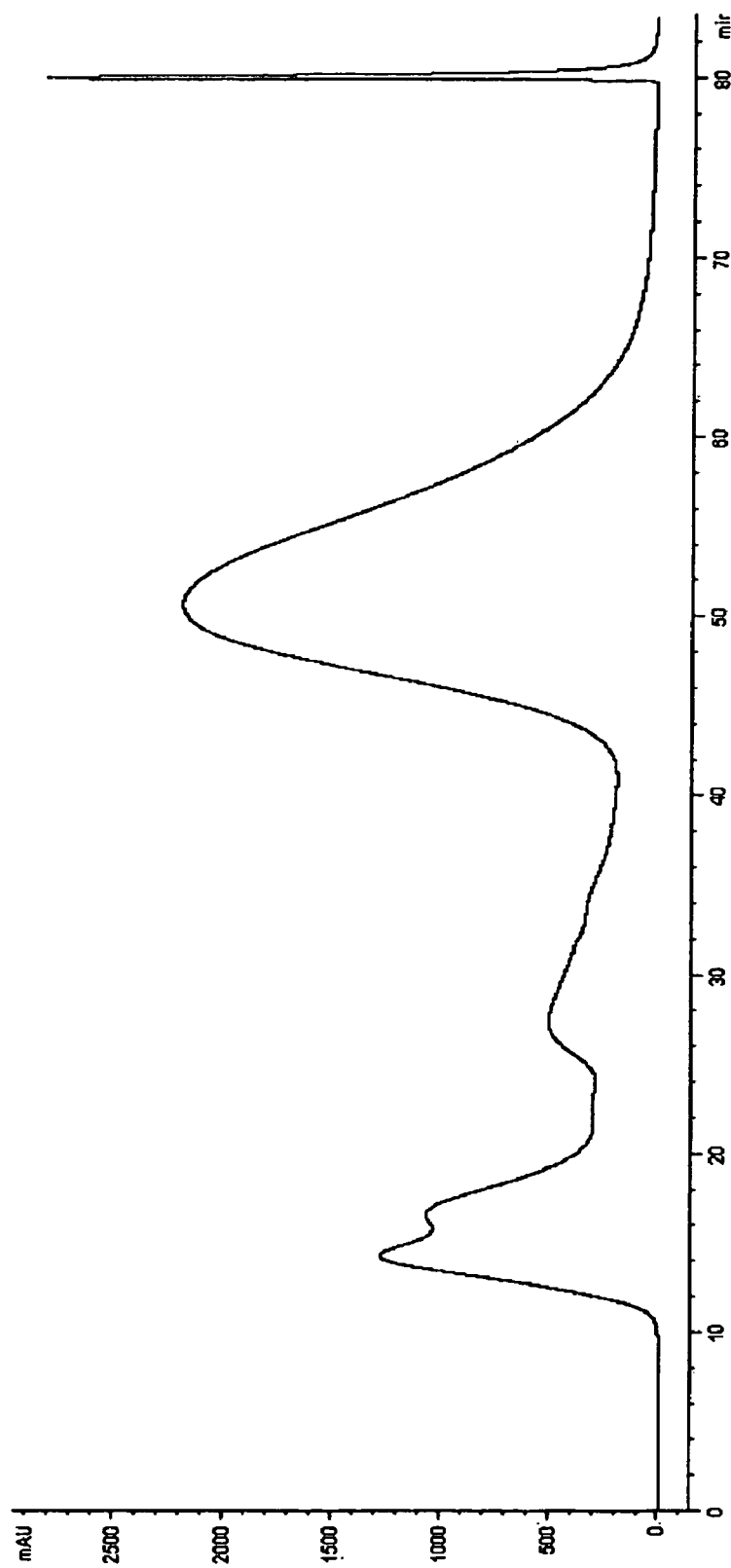

[Figure 7]
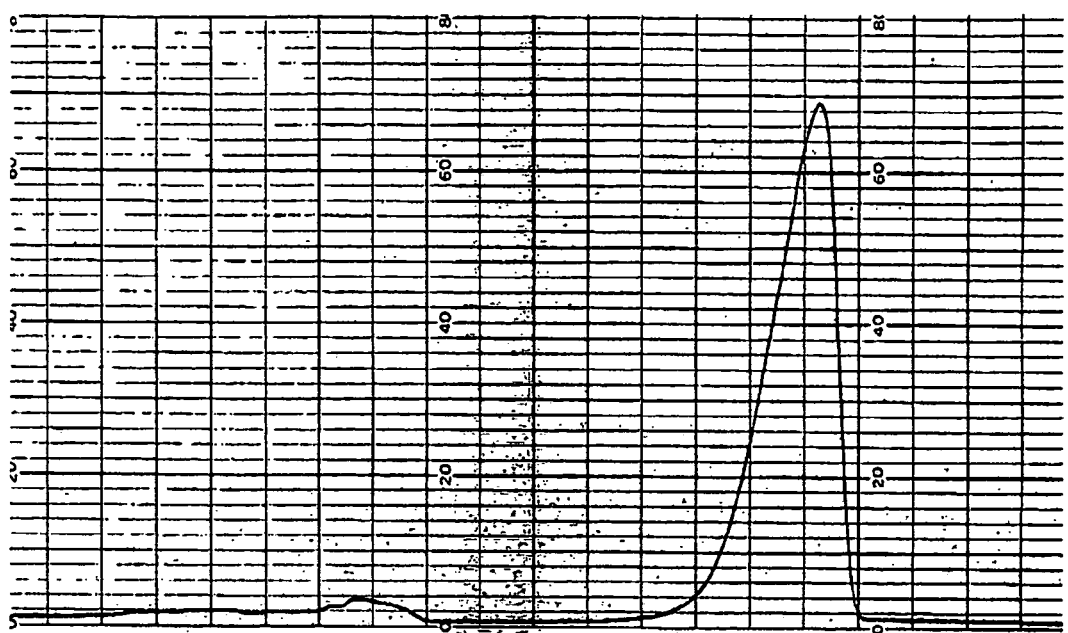

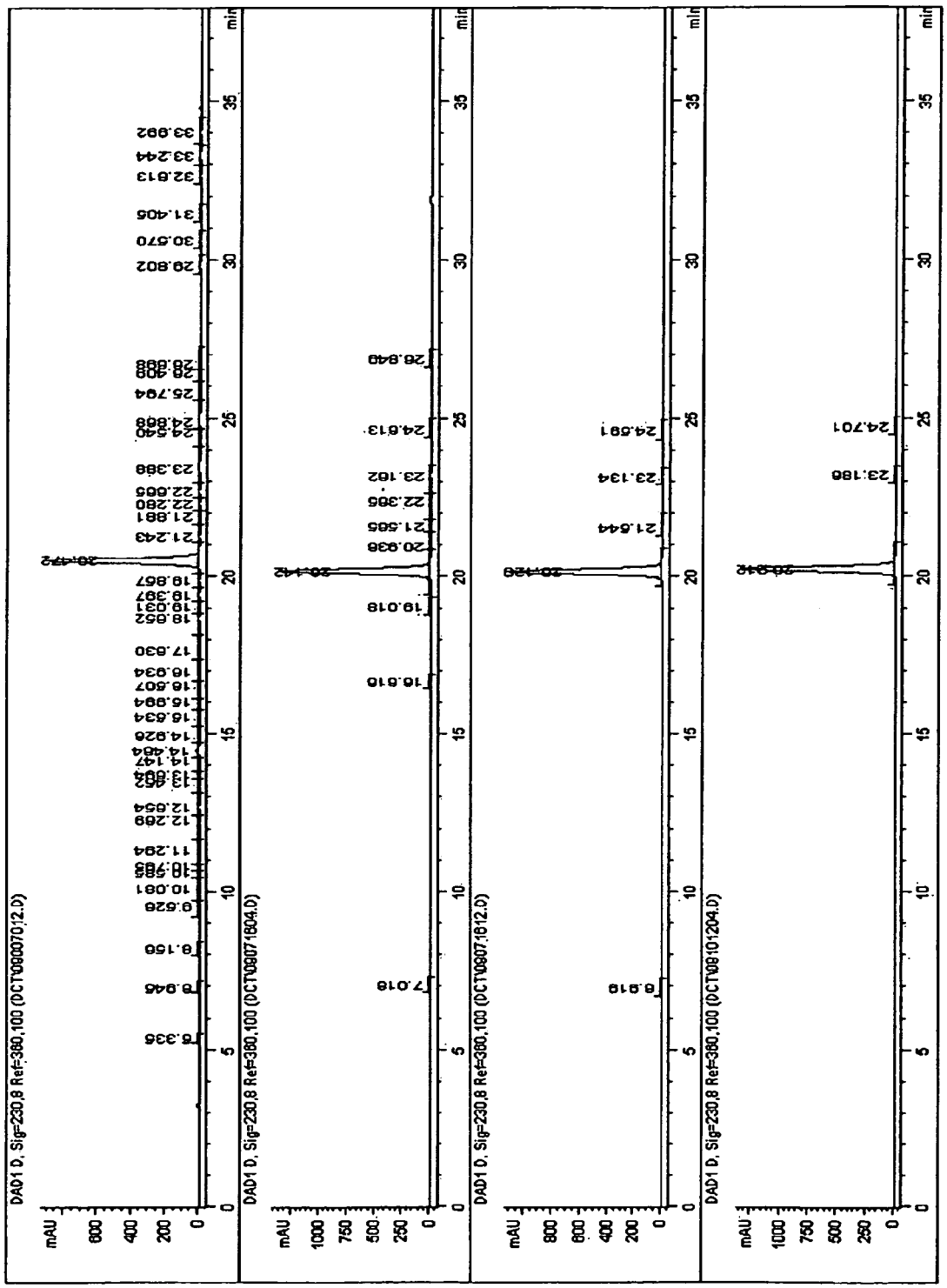
[Figure 8]

[Figure 9]
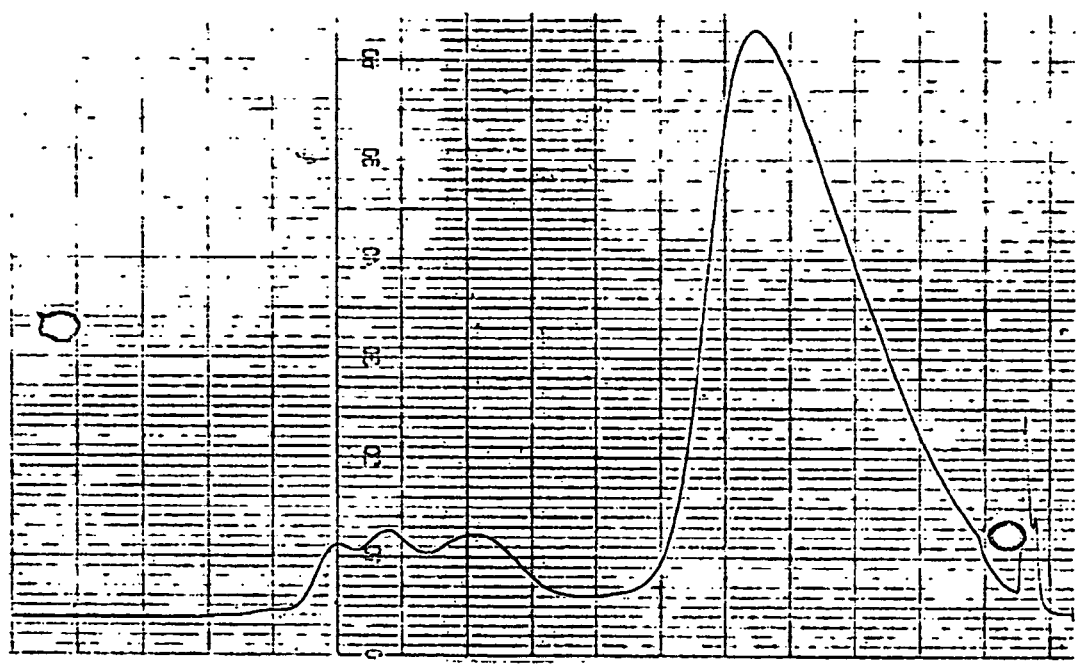
[Figure 10]
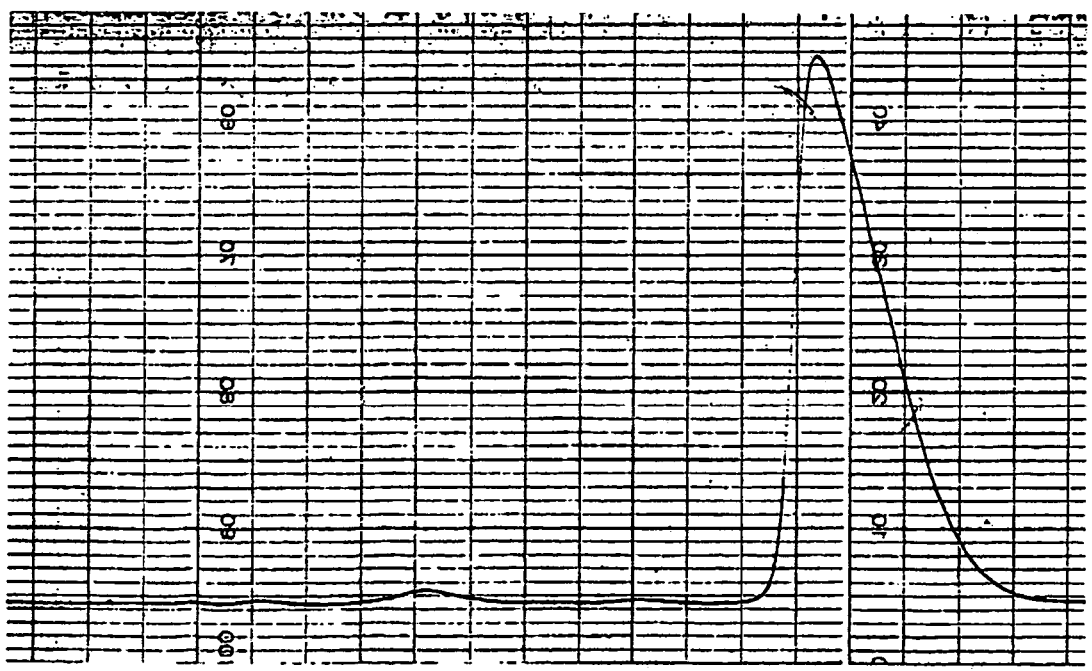

[Figure 11]
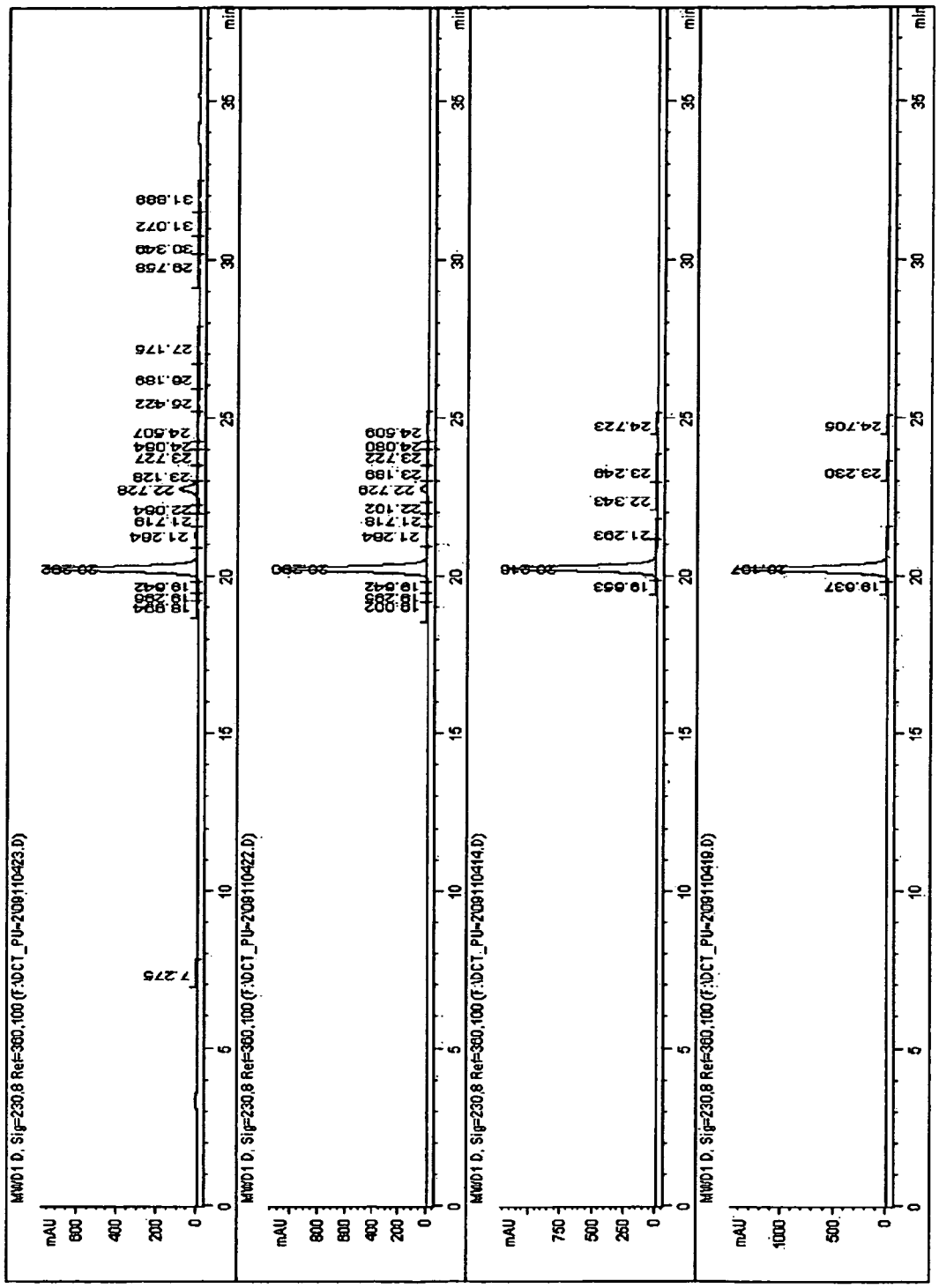

[Figure 12]
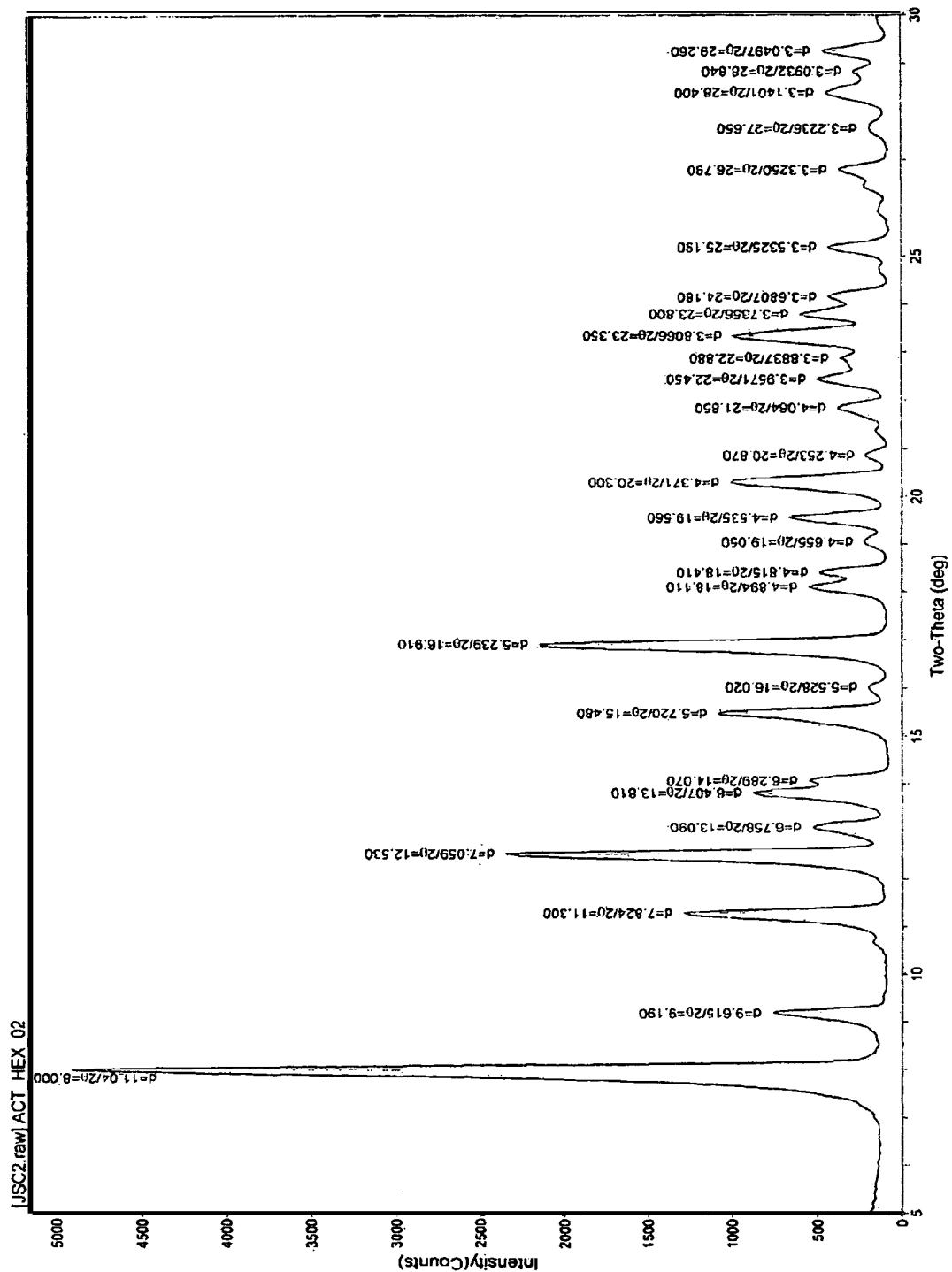

[Figure 13]
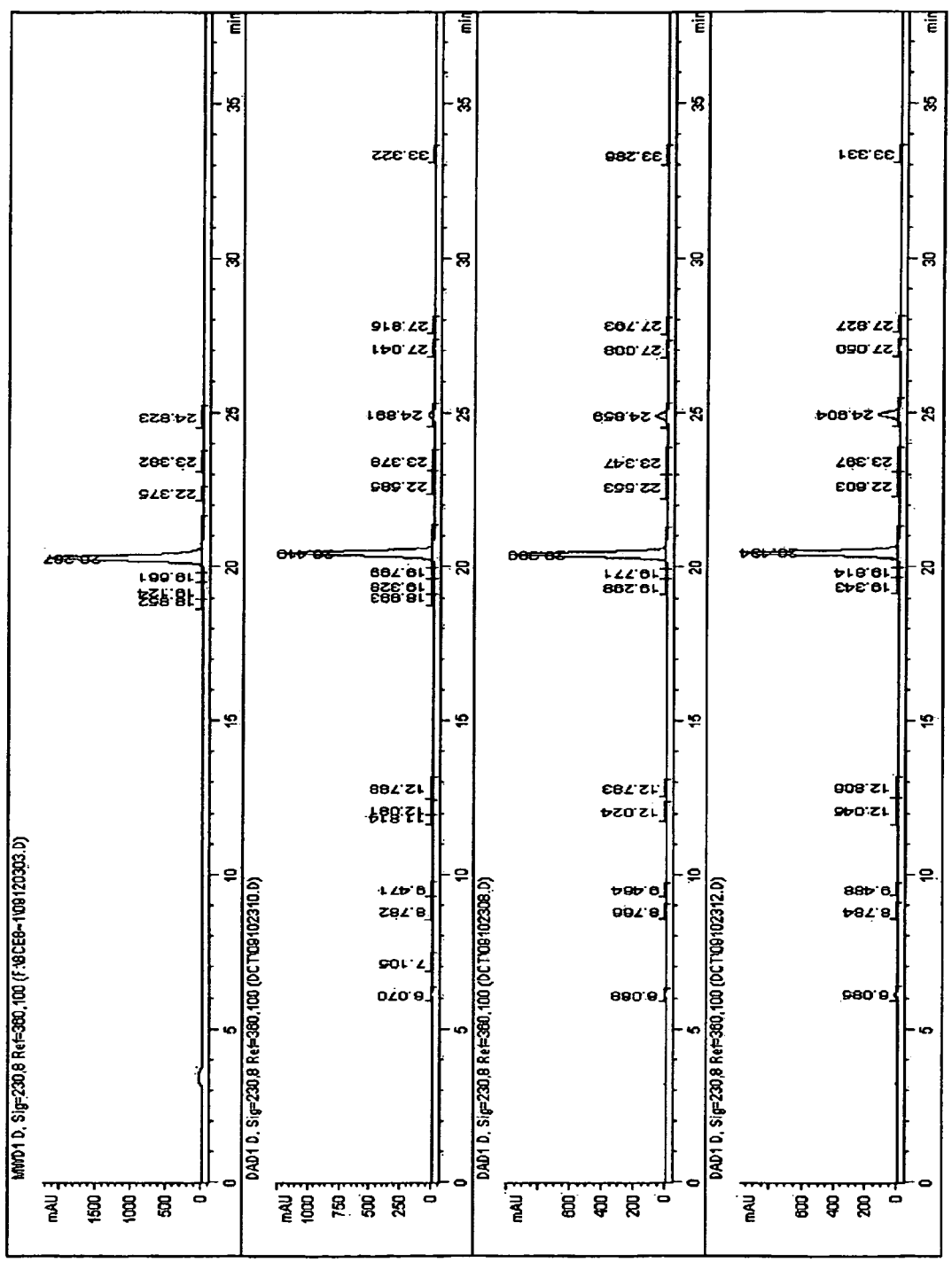

METHOD FOR PREPARING HIGHLY PURE ANHYDROUS CRYSTALLINE DOCETAXEL

CROSS-REFERENCE TO RELATED APPLICATIONS

This application is the U.S. National Phase of PCT/KR2010/009344 filed Dec. 27, 2010, which claims priority of Korean Patent Application 10-2009-0135668 filed Dec. 31, 2009.

FIELD OF THE INVENTION

The present invention relates to a method for preparing highly pure anhydrous crystalline docetaxel, more specifically, to a method for preparing anhydrous crystalline docetaxel having purity of 99.5% or more.

BACKGROUND OF THE INVENTION

Docetaxel, which belongs to taxoids, is an anti-cancer chemotherapeutic agent having a broad spectrum of anti-tumor and anti-leukemia activities. It is a semi-synthesized anti-cancer drug obtained by chemical modification of 10-deactylbaccatin III which is extracted from leaves and barks of Europe or India Yew tree, and has been approved as a marketable therapeutic agent against breast cancer and ovarian cancer, etc. in many countries including Europe.

Although a method of recrystallization using acetone and hexane, and a method of recrystallization using acetonitrile and purified water are currently known to prepare anhydrous crystalline docetaxel by recrystallizing semi-synthesized docetaxel, a method of recrystallization using dichloromethane and hexane, these methods lead to anhydrous crystalline docetaxel with markedly low purity. Particularly, it is very important to increase purity of docetaxel for medical use.

Particularly, in the preparation of highly pure anhydrous crystalline docetaxel, it is difficult to remove impurities or residual solvents. During preparation of anhydrous crystalline docetaxel, stability of docetaxel is destroyed and impurities such as 7-epimer, i.e., 4-acetoxy-2α-benzoyloxy-5-β, 20-epoxy-1,7β,10β-trihydroxy-9-oxo-tac-11-ene-1 3-α-yl (2R,3S)-3-t-butoxycarbonylamino-2'-hydroxy-3-phenylpropionate are generated. Thus, it is very difficult to prepare highly pure anhydrous crystalline docetaxel.

Accordingly, there is a demand for development of a method for preparing highly pure anhydrous crystalline docetaxel having low impurity contents.

DETAILED DESCRIPTION OF THE INVENTION

Technical Problem

Accordingly, the present inventors have completed the invention by developing a method for preparing highly pure anhydrous crystalline docetaxel.

It is an object of the present invention to provide a method for preparing anhydrous crystalline docetaxel having purity of 99.5% or more comprising: (a) primarily purifying semi-synthesized docetaxel by low-pressure normal-phase chromatography; (b) secondarily purifying the primarily purified docetaxel by low-pressure reversed-phase chromatography; (c) adding acid in the concentration of 0.05% (v/v) to 10% (v/v) of docetaxel aliquot obtained after the secondary purification of docetaxcel of (b) to concentrate the secondarily purified docetaxel; and (d) recrystallizing the concentrated docetaxel of (c).

It is another object of the present invention to provide a method for preparing anhydrous crystalline docetaxel having purity of 99.5% or more comprising: (a) primarily purifying semi-synthesized docetaxel by low-pressure normal-phase chromatography; (b) secondarily purifying the primarily purified docetaxel by high-pressure reversed-phase chromatography; (c) adding acid in the concentration of 0.05% (v/v) to 10% (v/v) of docetaxel aliquot obtained after the secondary purification of docetaxcel of (b) to concentrate the secondarily purified docetaxel; and (d) recrystallizing the concentrated docetaxel of (c).

It is yet another object of the present invention to provide a method for preparing anhydrous crystalline docetaxel having purity of 99.5% or more comprising: (a) primarily purifying semi-synthesized docetaxel by low-pressure reversed-phase chromatography; (b) adding acid in the concentration of 0.05% (v/v) to 10% (v/v) of docetaxel aliquot obtained after the primary purification of docetaxcel of (a) to concentrate the primarily purified docetaxel (c) secondarily purifying the concentrated docetaxel by high-pressure normal-phase chromatography; and (d) recrystallizing the secondarily purified docetaxel of (c).

Technical Solution

To solve the above technical problems, the present invention provides a method for preparing anhydrous crystalline docetaxel having purity of 99.5% or more comprising: (a) primarily purifying semi-synthesized docetaxel by low-pressure normal-phase chromatography; (b) secondarily purifying the primarily purified docetaxel by low-pressure reversed-phase chromatography; (c) adding acid in the concentration of 0.05% (v/v) to 10% (v/v) of docetaxel aliquot obtained after the secondary purification of docetaxcel of (b) to concentrate the secondarily purified docetaxel; and (d) recrystallizing the concentrated docetaxel of (c).

The present invention also provides a method for preparing anhydrous crystalline docetaxel having purity of 99.5% or more comprising: (a) primarily purifying semi-synthesized docetaxel by low-pressure normal-phase chromatography; (b) secondarily purifying the primarily purified docetaxel by high-pressure reversed-phase chromatography; (c) adding acid in the concentration of 0.05% (v/v) to 10% (v/v) of docetaxel aliquot obtained after the secondary purification of docetaxcel of (b) to concentrate the secondarily purified docetaxel; and (d) recrystallizing the concentrated docetaxel of (c).

The present invention also provides a method for preparing anhydrous crystalline docetaxel having purity of 99.5% or more comprising: (a) primarily purifying semi-synthesized docetaxel by low-pressure reversed-phase chromatography; (b) adding acid in the concentration of 0.05% (v/v) to 10% (v/v) of docetaxel aliquot obtained after the primary purification of docetaxcel of (a) to concentrate the primarily purified docetaxel (c) secondarily purifying the concentrated docetaxel by high-pressure normal-phase chromatography; and (d) recrystallizing the secondarily purified docetaxel of (c).

Hereinafter, the present invention will be described in detail.

To prepare highly pure anhydrous crystalline docetaxel, the method of the present invention includes largely 3 combined processes, through which anhydrous crystalline docetaxel having purity of 99.5% or more may be prepared from semi-synthesized docetaxel. Specifically, comparing the purity HPLC results of semi-synthesized docetaxel sample as shown in FIG. 1 with the HPLC results of anhydrous crystalline docetaxel prepared according to the purification processes of the present invention as shown in FIGS. 5, 8 and 11, it can be seen that highly pure docetaxel having purity of 99.5% or more can be prepared according to the method of the present invention.

Particularly, to increase purification efficiency of the docetaxel aliquot obtained after performing low-pressure or high-pressure reversed-phase chromatography, the aliqoute is concentrated with the addition of acid to remove impurities included in the reversed-phase chromatography, thereby forming docetaxel precipitate with decreased impurity contents.

The aliquot refers to a fraction including docetaxel obtained by the chromatography, and the obtaining method thereof may be easily determined by one of ordinary skill in the art.

The low-pressure, although not limited thereto, is preferably 5 psi to 1000 psi, and the high-pressure, although not limited thereto, is preferably 1500 psi to 4000 psi.

Hereinafter, the present invention will be explained according to processes in more detail.

1. Method for Preparing Highly Pure Anhydrous Crystalline Docetaxel I (a) Primary Purification of Semi-Synthesized Docetaxel by Tow-Pressure Normal-Phase Chromatography First, semi-synthesized docetaxel is purified by low-pressure normal-phase chromatography.

In case the low-pressure normal-phase chromatography is performed, although not limited thereto, a developing solvent selected from the group consisting of C1-2 halogenated alkanes, a C1-6 organic solvent, and a combination thereof may be preferably used. The C1-2 halogenated alkanes may include dichloromethane, chloroform, and a combination thereof, and the C1-6 organic solvent may include methanol, benzene, aceton, hexane, ethylacetate, and a combination thereof. More preferably, isocratic or step elution may be used, and 1.0% (v/v) to 20% (v/v) of a methanol/dichloromethane mixed solution (i.e., methanol(v):dichloromethane(v)=1.0:99 to 20:80), more preferably 2.5% (v/v) to 10% (v/v) of a methanol/dichloromethane mixed solution (i.e., methanol(v):dichloromethane(v)=2.5:97.5 to 10:90) may be used as the developing solvent.

Any method known in the art may be used to perform the low-pressure normal-phase chromatography, and preferably, silica gel 60(63~200 μm) may be used as column filler.

Through this process, semi-synthesized docetaxel (purity 45%) may be purified to purity of about 94%.

(b) Secondary Purification of the Primarily Purified Docetaxel by Low-Pressure Reversed-Phase Chromatography The docetaxel having purity of 90% or more, obtained in the step (a) is secondarily purified by low-pressure reversed-phase chromatography.

In case the low-pressure reversed-phase chromatography is performed, although not limited thereto, a developing solvent selected from the group consisting of a C1-3 organic solvent, purified water, and a combination thereof may be preferably used. The C1-3 organic solvent may include C1-3 alcohol, acetonitrile, and a combination thereof, and the alcohol may include methanol, ethanol, propanol, and a combination thereof. More preferably, isocratic or step elution may be used, and 30% (v/v) to 90% (v/v) of a methanol/purified water mixed solution (i.e., methanol(v):purified water(v)=30:70 to 90:10), preferably 60% (v/v) to 85% (v/v) of a methanol/ purified water mixed solution (i.e., methanol(v):purified water(v)=60:40 to 85:15) may be preferably used.

Any method known in the art may be used to perform the low-pressure normal-phase chromatography, and common hydrophobic resin such as 63~200 μm ODS(Octadecylsilylated, C18), C8 or C4 and the like may be preferably used as column filler.

Through this process, semi-synthesized docetaxel (purity 45%) may be purified to purity of about 99.4%.

(c) Concentration of the Secondarily Purified Docetaxel

Acid is added to the aliquot of docetaxel having purity of 99.4%, obtained in (b), to concentrate the secondarily purified docetaxel.

In case concentration is performed using acid to remove the organic solvent, although not limited thereto, concentration may be performed preferably at 35° C. to 60° C., more preferably at 40 to 50° C., and concentration time may be 1 to 10 hours.

The acid, although not limited thereto, may include acetic acid, formic acid, trifluoroacetic acid, and a combination thereof. To the aliquot of docetaxel obtained in (b), 0.05% (v/v) to 10% (v/v), more preferably 0.2% (v/v) to 5% (v/v) of acid may be added to concentrate.

After the concentration, if necessary, the product may be dried under reduced pressure to obtain dry solid substance.

Through this process, semi-synthesized docetaxel (purity 45%) may be purified to purity of about 99.5% or more.

(d) Recrystallization of the Concentrated Docetaxel

The docetaxel having purity of 99.5% or more, obtained in (c) may be recrystallized to prepare anhydrous crystalline docetaxel.

The recrsytallization solvent, although not limited thereto, may include acetone, hexane, and a combination thereof. More preferably, hexane may be added after dissolving the docetaxel obtained in (c) in acetone to perform recrystallizatoin. The acetone, although not limited thereto, may be preferably introduced so that docetaxel concentration may become 1% (w/v) to 30% (w/v), and the hexane may be introduced in a volume of 1 to 10 times of the amount of acetone introduced.

2. Method for Preparing Highly Pure Anhydrous Crystalline Docetaxel II (a) Primary Purification of Semi-Synthesized Docetaxel by Low-Pressure Normal-Phase Chromatography The primary purification by low-pressure normal-phase chromatography may be performed by the same process as described in (a) of the 'Method for preparing highly pure anhydrous crystalline docetaxel I'.

(b) Secondary Purification of the Primarily Purified Docetaxel by High-Pressure Reversed-Phase Chromatography The docetaxel having purity of 90% or more, obtained in (a), is secondarily purified by high-pressure reversed-phase chromatography.

The secondary purification by high-pressure reversed-phase chromatography may be performed by the same process as described in (b) of the 'Method for preparing highly pure anhydrous crystalline docetaxel I', except for a pressure condition. As column filler, common hydrophobic resin such as 5 to 100 μm, preferably 10 to 50 μm ODS (Octadecylsilylated, C18), C8 or C4 and the like may be preferably used.

Through this step, aliquot of docetaxel having purity of about 99.4% may be prepared.

(c) Concentration of the Secondarily Purified Docetaxel Using Acid

Acid is added to the aliquot of docetaxel obtained in (b) to concentrate it.

The concentration process using acid may be performed by the same manner as described in (c) of the 'Method for preparing highly pure anhydrous crystalline docetaxel I'.

Through this process, docetaxel having purity of 99.7% or more may be obtained.

(d) Recrystallization of the Concentrated Docetaxel

The docetaxel having purity of 99.7% or more, obtained in (c), may be recrystallized to prepare anhydrous crystalline docetaxel.

The recrystallization may be performed by the same process as described in (d) of the 'Method for preparing highly pure anhydrous crystalline docetaxel I'.

Through this process, docetaxel having purity of 99.8% or more may be obtained.

3. Method for Preparing Highly Pure Anhydrous Crystalline Docetaxel III (a) Primary Purification of Semi-Synthesized Docetaxel by Low-Pressure Reversed-Phase Chromatography Semi-synthesized docetaxel may be primarily purified by low-pressure reversed-phased chromatography.

The primary purification by low-pressure reversed-phased chromatography may be performed by the same process as described in (b) of the 'Method for preparing highly pure anhydrous crystalline docetaxel I'.

Through this process, aliquot of docetaxel having purity of about 80 to 84% may be separated.

(b) Concentration of the Primarily Purified Docetaxel with Acid

Acid is added to the docetaxel aliquot obtained in (a) to concentrate it.

The concentration process with acid may be performed by the same manner as described in (c) of 'Method for preparing highly pure anhydrous crystalline docetaxel I'.

Through this process, docetaxel having purity of 90 to 94% may be obtained.

(c) Secondary Purification of the Concentrated Docetaxel by High-Pressure Normal-Phase Chromatography The docetaxel obtained in (b) may be secondarily purified by high-pressure normal-phase chromatography.

The secondary purification by high-pressure normal-phase chromatography may be performed by the same manner as described in (a) of 'Method for preparing highly pure anhydrous crystalline docetaxel I'. However, as column filler, silica gel 20 μm may be preferably used.

Through this process, docetaxel having purity of 99.5% to 99.6% may be obtained.

(d) Recrystallization of the Secondarily Purified Docetaxel

The secondarily purified docetaxel in (c) may be recrystallized to prepare anhydrous crystalline docetaxel.

The recrystallization may be performed as described in 1(d).

Through this process, anhydrous crystalline docetaxel having purity of 99.7 to 99.8% or more may be obtained.

The results of the methods for preparing highly pure anhydrous crystalline docetaxel having purity of 99.5% or more with yield of 77% to 88% are summarized in the following Table 1.

TABLE 1

|  | Docetaxel purity (%) | Recovery rate (%) |
|---|---|---|
| Method for preparing highly pure anhydrous crystalline docetaxel I | | |
| Starting material: semi-synthesized docetaxel | 40-45 | 100 |
| Low-pressure normal-phase chromatography | 90-94 | 94-97 |
| Low-pressure reversed-phase chromatography | 99.0-99.4 | 93-97 |
| Concentration by acid | 99.5-99.7 | 98-99 |

TABLE 1-continued

|  | | |
|---|---|---|
| Recrystallization | 99.8-99.9 | 92-95 |
| Total | 99.8-99.9 | 78-88 |
| Method for preparing highly pure anhydrous crystalline docetaxel II | | |
| Starting material: semi-synthesized docetaxel | 40-45 | 100 |
| Low-pressure normal-phase chromatography | 90-94 | 94-97 |
| High-pressure reversed-phase chromatography | 99.0-99.4 | 92-95 |
| Concentration by acid | 99.5-99.7 | 98-99 |
| Recrystallization | 99.8-99.9 | 92-95 |
| Total | 99.8-99.9 | 77-86 |
| Method for preparing highly pure anhydrous crystalline docetaxel III | | |
| Starting material: semi-synthesized docetaxel | 40-45 | 100 |
| Low-pressure reversed-phase chromatography | 80-84 | 93-96 |
| Concentration by acid | 90-94 | 97-99 |
| High-pressure normal-phase chromatography | 99.0-99.5 | 94-96 |
| Recrystallization | 99.8-99.9 | 92-95 |
| Total | 99.8-99.9 | 78-86 |

Purity and recovery rates of docetaxel may be measured by any method known in the art, and preferably using HPLC analysis as described in the following Table 2.

TABLE 2

| | |
|---|---|
| Instrument | Hewlett-Packard 1100 HPLC |
| Column | Octadecylsilica (C18) 4.6 × 250 mm, 5 micro |
| Column temperature | 35° C. |
| Mobile phase | acetonitrile:water = 35:65% (v/v); concentration gradient |
| Flow rate | 1 ml/min |
| Amount of injection | 10 ul |
| Detector | UV (230 nm) |

According to the method for preparing highly pure anhydrous crystalline doceta xel of the present invention, anhydrous crystalline docetaxel that has purity of 99.5% or more and has remarkably lower residual solvent content than the standard for residual s olvents in drugs can be prepared, implying that it may be a promising source as an antic ancer agent.

BRIEF DESCRIPTION OF DRAWINGS

FIG. 1 shows the HPLC analysis result of purity of sample before purification process, i.e., semi-synthesized docetaxel.

FIG. 2 shows the HPLC analysis result of purity of docetaxel in Example <1-4-2>.

FIG. 3 shows the result of aliquot chromatogram of low-pressure normal-phase chromatography of Example <1-1> (X axis: Time (min.), Y axis: Response (mAU)).

FIG. 4 shows the result of aliquot chromatogram of low-pressure reversed-phase chromatography of Example <1-2> (X axis: Time (min.), Y axis: Response (mAU)).

FIG. 5 shows the HPLC results analyzing purifies of Examples <1-1>, <1-2>, <1-3-2> and <1-4-2> in order, viewed from the top.

FIG. 6 shows the result of aliquot chromatogram of low-pressure normal-phase chromatography of Example <2-1>.

FIG. 7 shows the result of aliquot chromatogram of high-pressure reversed-phase chromatography of Example <2-2> (X axis: Time (min.), Y axis: Response (mAU)).

FIG. 8 shows the HPLC results analyzing purities of Examples <2-1>, <2-2>, <2-3>, <2-4> in order, viewed from the top.

FIG. 9 shows the result of aliquot chromatogram of low-pressure reversed-phase chromatography of Example <3-1-1> (X axis: Time (min.), Y axis: Response (mAU)).

FIG. 10 shows the result of aliquot chromatogram of high-pressure normal-phase chromatography of Example <3-3> (X axis: Time (min.), Y axis: Response (mAU)).

FIG. 11 shows the HPLC results analyzing purifies of Examples <3-1-1>, <3-2-1>, <3-3>, <3-4> in order, viewed from the top.

FIG. 12 shows the XRD result of Example <1-4-2>.

FIG. 13 shows the HPLC results comparing purity of Example <1-2> with purities of Comparative Examples 1, 2 and 3 in order, viewed from the top.

EXAMPLES

The present invention will be explained in detail with reference to the following examples and experiments.

However, the following examples and experiments are only to illustrate the present invention, and the scope of the present invention is not limited thereto.

Example 1

Method for Preparing Highly Pure Anhydrous Crystalline Docetaxel I

<1-1> Low-Pressure Normal-Phase Chromatography 180 g of semi-snythesized docetaxel (purity 45%) was completely dissolved in 1000 ml of dichloromethane to prepare a sample. Using a column filled with silica gel 60(63~200 μm), chromatography was conducted under operation conditions as described in the following Table 3.

TABLE 3

| Kind of column | Silica gel 60 (63~200 μm), inner diameter 10 cm, length 90 cm |
|---|---|
| Column temperature | Room temperature |
| Mobile phase | dichloromethane:methanol = 97.5%:2.5% (v/v); isocratic |
| Flow rate | 544 ml/min. |
| Sample injection | Dry solid substance 180 g/dichloromethane 1000 ml |
| Detector | UV (230 nm) |

About 40 minutes after injecting the sample, an active fraction of docetaxel was aliquoted, and then, concentrated under reduced pressure at a temperature of 45° C. to concentrate the aliquot of docetaxel. After the concentration was completed, the concentrate was vacuum-dried at a temperature of 45° C. under reduced pressure of 760 mmHg for 1 day.

The amount of recovered dry solid substance was 98 g, purify was 94%, and the yield was 97%.

<1-2> Low-Pressure Reversed-Phase Chromatography

After 98 g of the dry solid substance of Example <1-1> was completely dissolved in 1100 ml of methanol, 275 ml of purified water was added to prepare a sample. Chromatography was conducted using a column filled with hydrophobic resin 63~200 μm ODS (Octadecylsilylated, C18) under operation conditions as described in the following Table 4.

TABLE 4

| Kind of column | octadecylsilica (c18, 100 μm), inner diameter 10 cm, length 90 cm |
|---|---|
| Column temperature | Room temperature |
| Mobile phase | methanol:purified water = 65.5%:34.5% (v/v); isocratic |

TABLE 4-continued

| Flow rate | 544 ml/min. |
|---|---|
| Sample injection | Dry solid substance 98 g/methanol 1100 ml, purified water 275 ml |
| detector | UV (230 nm) |

About 45 minutes after injecting the sample, an active fraction of docetaxel was aliquoted.

The aliquot of docetaxel was 3510 ml, purity was 99.4%, and yield was 97%.

<1-3> Concentration by Acid 1-3-1. Concentration by Acid (0.2%)

To 2000 ml of the docetaxel aliquot of Example <1-2> (docetaxel amount 43 g, purity 99.4), 4 ml of acetic acid (0.2% (v/v) was added, and the mixture was concentrated under reduced pressure at a temperature of 45° C. The maximum amount of methanol was removed by the concentration under reduced pressure to induce precipitation of docetaxel, and the precipitate was filtered under reduced pressure using a filter paper (Whatman No. 42). Docetaxel precipitate obtained after the filtration under reduced pressure was vacuum-dried at a temperature of 45° C. under reduced pressure of 760 mmHg for 2 days.

The amount of recovered dry solid substance was 41 g, purity was 99.7%, and the yield was 98%.

1-3-2. Concentration by Acid (1%)

To 350 ml of docetaxel aliquot of Example <1-2> (docetaxel amount 7.6 g, purity 99.4), 3.5 ml of acetic acid (1% (v/v)) was added, and the mixture was concentrated under reduced pressure at a temperature of 45° C. The maximum amount of methanol was removed by the concentration under reduced pressure to induce precipitation of docetaxel, and the precipitate was filtered under reduced pressure using a filter paper (Whatman No. 42). The docetaxel precipitate obtained after filtration under reduced pressure was vacuum-dried at a temperature of 45° C. under reduced pressure of 760 mmHg for 2 days.

The amount of recovered dry solid substance was 7.5 g, purity was 99.6%, and the yield was 98%.

1-3-3. Concentration by Acid (5%)

To 350 ml of the docetaxel aliquot of Example <1-2> (docetaxel amount 7.6 g, purity 99.4), 17.5 ml of acetic acid (5% (v/v)) was added, and the mixture was concentrated under reduced pressure at a temperature of 45° C. The maximum amount of methanol was removed by the concentration under reduced pressure to induce precipitation of docetaxel, and the generated precipitate was filtered under reduced pressure using a filter paper (Whatman No. 42). The docetaxel precipitate obtained after filtration under reduced pressure was vacuum dried at a temperature of 45° C. under reduced pressure of 760 mmHg for 2 days.

The amount of recovered dry solid substance was 7.4 g, purity was 99.7%, and the yield was 98%.

<1-4> Recrystallization 1-4-1. Acetone:Hexane=1:1.8 (v/v)

7.17 g of the dry solid substance having purity of 99.7% of Example <1-3-1> was completely dissolved in 72 ml of acetone at room temperature, and then, 129.6 ml of hexane was added while agitating for 10 minutes, and the mixture was stored at a temperature of 4° C. for 12 hours to induce recrystallization. After 12 hours, filtration under reduced pressure was conducted using a filter paper (Whatman No. 42). The docetaxel obtained by the filtration under reduced pressure was vacuum-dried at a temperature of 45 under reduced pressure of 760 mmHg for 6 days.

Anhydrous crystalline docetaxel was obtained with the amount of recovered dry solid of 6.7 g, purity of 99.8%, and yield of 93%.

1-4-2. Acetone:Hexane=1:2.0 (v/v)

7.2 g of the dry solid substance having purity of 99.6% of Example <1-3-2> was completely dissolved in 72 ml of acetone at room temperature, and then, 144 ml of hexane was added while agitating for 10 minutes, and the mixture was stored at a temperature of 4° C. for 12 hours to induce recrystallization. After 12 hours, filtration under reduced pressure was conducted using a filter paper (Whatman No. 42). The docetaxel obtained by the filtration under reduced pressure was vacuum-dried at a temperature of 45° C. under reduced pressure of 760 mmHg for 6 days.

Anhydrous crystalline docetaxel was obtained with the amount of recovered dry solid of 6.9 g, purity of 99.8%, and yield of 96%.

1-4-3. Acetone:Hexane=1:2.3 (v/v)

7.3 g of the dry solid substance having purity of 99.7% of Example <1-3-3> was completely dissolved in 72 ml of acetone at room temperature, and then, 165.6 ml of hexane was added while agitating for 10 minutes, and the mixture was stored at a temperature of 4° C. for 12 hours to induce recrystallization. After 12 hours, filtration under reduced pressure was conducted using a filter paper (Whatman No. 42). The docetaxel obtained by the filtration under reduced pressure was vacuum-dried at a temperature of 45° C. under reduced pressure of 760 mmHg for 6 days.

Anhydrous crystalline docetaxel was obtained with the amount of recovered dry solid of 6.9 g, purity of 99.8%, and yield of 94%.

<1-5> Summarization of Results of Example 1

Purities and yields according to each process of Example 1 are summarized in the following Table 5.

TABLE 5

| | docetaxel purity (%) | 7-epimer (%) | Recovery rate (%) |
|---|---|---|---|
| Starting material: semi-synthesized docetaxel | 45 | 10.045 | 100 |
| Low-pressure normal-phase chromatography | 94 | 2.101 | 97 |
| Low-pressure reversed-phase chromatography | 99.4 | 0.050 | 97 |
| Concentration by acid (0.2%) | 99.7 | 0.031 | 98 |
| recrystallization[acetone:hexane = 1:1.8 (v/v)] | 99.8 | 0.011 | 93 |
| Total | 99.8 | 0.011 | 86 |
| Starting material: semi-synthesized docetaxel | 45 | 10.045 | 100 |
| Low-pressure normal-phase chromatography | 94 | 2.101 | 97 |
| Low-pressure reversed-phase chromatography | 99.4 | 0.050 | 97 |
| Concentration by acid (1%) | 99.6 | 0.021 | 98 |
| recrystallization[acetone:hexane = 1:2.0 (v/v)] | 99.8 | 0.017 | 96 |
| Total | 99.8 | 0.017 | 88 |
| Starting material: semi-synthesized docetaxel | 45 | 10.045 | 100 |
| Low-pressure normal-phase chromatography | 94 | 2.101 | 97 |
| Low-pressure reversed-phase chromatography | 99.4 | 0.050 | 97 |
| Concentration by acid (5%) | 99.7 | 0.031 | 98 |
| recrystallization [acetone:hexane = 1:2.3 (v/v)] | 99.8 | 0.014 | 94 |
| Total | 99.8 | 0.014 | 86 |

Residual solvent contents of Example 1 are described in the following Table 6.

TABLE 6

| | Methanol (ppm) | Dichloro-methane (ppm) | Acetone (ppm) | Hexane (ppm) | Acetic acid (ppm) |
|---|---|---|---|---|---|
| Limit concentration standard (ICH guidline*) | 3,000 | 600 | 5,000 | 290 | 5,000 |
| Example 1-4-1 | 35 | 26 | 20 | 58 | 25 |
| Example 1-4-2 | 42 | 34 | 27 | 64 | 31 |
| Example 1-4-3 | 37 | 28 | 32 | 61 | 48 |

*ICH guideline: International conference on Harmonization, standard guideline for residual solvents acceptable in drugs.

As described above, it can be seen that anhydrous crystalline docetaxel having purity of 99.5% or more may be prepared by sequentially conducting low-pressure normal-phase chromatography on semi-synthesized docetaxel, low-pressure reversed-phase chromatography, concentration by acid, and recrystallization, and that the prepared docetaxel has remarkably lower residual solvent contents than the standard for residual solvents in drugs, implying that it may be a promising source as an anticancer agent.

Example 2

Method for Preparing Highly Pure Anhydrous Crystalline Docetaxel II

<2-1> Low-Pressure Normal-Phase Chromatography 0.6 g of semi-snythesized docetaxel (purity 45%) was completely dissolved in 3.2 ml of dichloromethane to prepare a sample. Using a column filled with silica gel 60(63~200 μm), chromatography was conducted under operation conditions as described in the following Table 7.

TABLE 7

| Kinds of column | Silica gel 60 (63~200 μm), inner diameter 1 cm, length 90 cm |
|---|---|
| Column temperature | Room temperature |
| Mobile phase | dichloromethane:methanol = 97.5%:2.5% (v/v); isocratic |
| Flow rate | 1.1 ml/min. |
| Sample injection | docetaxel 0.6 g/dichloromethane 3.2 ml |
| Detector | UV (230 nm) |

About 40 minutes after injecting the sample, an active fraction of docetaxel was aliquoted, and then, concentrated under reduced pressure at a temperature of 45° C. to concentrate the aliquot of docetaxel. After the concentration was completed, the concentrate was vacuum-dried at a temperature of 45° C. under reduced pressure of 760 mmHg for 1 day.

The amount of recovered dry solid substance was 0.34 g, purify was 94%, and the yield was 96%.

<2-2> High-Pressure Reversed-Phase Chromatography

After 0.34 g of the dry solid substance of Example <2-1> was completely dissolved in 2.7 ml of methanol, 1.1 ml of purified water was added to prepare a sample. Chromatography was conducted using a column filled with hydrophobic resin octadecylsilylated (C18, 20 μm) under operation conditions as described in the following Table 8.

TABLE 8

| Kinds of column | octadecylsilica (c18, 20 μm), inner diameter 1 cm, length 90 cm |
|---|---|
| Column temperature | Room temperature |
| Mobile phase | Methanol:purified water = 70%:30% (v/v); isocratic |

TABLE 8-continued

| | |
|---|---|
| Flow rate | 5.4 ml/min. |
| Sample injection | docetaxel 0.34 g/methanol 2.7 ml, purified water 1.1 ml |
| Detector | UV (230 nm) |

About 45 minutes after the sample injection, an active fraction of docetaxel was aliquoted.

The docetaxel aliquot was 105 ml with purity of 99.4% and yield of 97%.

<2-3> Concentration by Acid (1%)

To 105 ml of the docetaxel aliquot of Example <2-2>, 1.05 ml of acetic acid (1% (v/v) was added, and the mixture was concentrated under reduced pressure. Methanol was maximally removed by the concentration under reduced pressure to induce precipitation of docetaxel, and the precipitate was filtered under reduced pressure using a filter paper (Whatman No. 2). Docetaxel precipitate obtained after the filtration under reduced pressure was vacuum-dried at a temperature of 45° C. under reduced pressure of 760 mmHg for 1 day.

The amount of recovered dry solid substance was 0.25 g, purity was 99.8%, and yield was 98%.

<2-4> Recrystallization 0.25 g of docetaxel having purity of 99.8% of Example <2-3> was completely dissolved in 2.5 ml of acetone at room temperature, and then, 2.75 ml of hexane (2.3 times the amount of acetone) was added while agitating for 10 minutes, and the mixture was stored at a temperature of 4° C. for 12 hours to induce recrystallization. After 12 hours, filtration under reduced pressure was conducted using a filter paper (Whatman No. 42). The docetaxel obtained by the filtration under reduced pressure was vacuum-dried at a temperature of 45° C. under reduced pressure of 760 mmHg for 6 days.

Anhydrous crystalline docetaxel was obtained in an amount of recovered dry solid substance of 0.22 g with purity of 99.9% and yield of 92%.

<2-5> Summarization of Results of Example 2

Purities and yields according to each process in Example 2 are described in the following Table 9.

TABLE 9

| | docetaxel purity (%) | 7-epimer (%) | Recovery rate (%) |
|---|---|---|---|
| Starting material: semi-synthesized docetaxel | 45 | 10.045 | 100 |
| Low-pressure normal-phase chromatography | 94 | 1 | 96 |
| High-pressure reversed-phase chromatography | 99.4 | 0.021 | 95 |
| Concentration by acid (1%) | 99.8 | 0.018 | 96 |
| Recrystallization [acetone:hexane = 1:2.3 (v/v)] | 99.9 | 0.010 | 92 |
| Total | 99.9 | 0.010 | 80 |

Residual solvent contents of Example 2 are described in the following Table 10.

TABLE 10

| | Methanol (ppm) | dichloromethane (ppm) | Acetone (ppm) | Hexane (ppm) | Acetic acid (ppm) |
|---|---|---|---|---|---|
| Limit concentration standard (ICH guideline*) | 3,000 | 600 | 5,000 | 290 | 5,000 |
| Recrystallization | 45 | 30 | 25 | 48 | 35 |

As described above, it can be seen that anhydrous crystalline docetaxel having purity of 99.5% or more may be prepared by sequentially conducting low-pressure normal-phase chromatography on semi-synthesized docetaxel, high-pressure reversed-phase chromatography, concentration by acid, and recrystallization, and that the prepared docetaxel has remarkably lower residual solvent contents than the standard for residual solvents in drugs, implying that it may be a promising source as an anticancer agent.

Example 3

Method for Preparing Highly Pure Anhydrous Crystalline Docetaxel III

<3-1> Low-Pressure Reversed-Phase Chromatography 3-1-1. Methanol:Purified Water=65.5:34.5(v/v)

0.6 g of semi-snythesized docetaxel (purity 45%) was completely dissolved in 4.8 ml of methanol, and 1.2 ml of purified water was added to prepare a sample. Using a column filled with octadecylsilica (c18, 100 um), chromatography was conducted under operation conditions as described in Table 4 shown above. About 45 minutes after the sample injection, an active fraction of docetaxel was aliquoted.

The docetaxel aliquot was 120 ml, purity was 84%, and yield was 95%.

3-1-2. Methanol:Purified Water=67.5:32.5(v/v)

0.6 g of semi-synthesized docetaxel (purity 45%) was completely dissolved in 4.8 ml of methanol, and then, 1.2 ml of purified water was added to prepare a sample. Chromatography was conducted using a column filled with octadecylsilca (c18, 100 um) under operation conditions as described in Table 4 shown above. About 45 minutes after the sample injection, an active fraction of docetaxel was aliquoted.

The docetaxel aliquot was 105 ml, purity was 84%, and yield was 94%.

3-1-3. Methanol:Purified Water=70:30(v/v)

0.6 g of semi-synthesized docetaxel (purity 45%) was completely dissolved in 4.8 ml of methanol, and then, 1.2 ml of purified water was added to prepare a sample. Chromatography was conducted using a column filled with octadecylsilca (c18, 100 um) under operation conditions as described in Table 4 shown above. About 45 minutes after the sample injection, an active fraction of docetaxel was aliquoted.

The docetaxel aliquot was 85 ml, purity was 80%, and yield was 96%.

The Example <3-1> is summarized in the following Table 11.

TABLE 11

| | Example | | |
|---|---|---|---|
| | 3-1-1 | 3-1-2 | 3-1-3 |
| Kinds of column | octadecylsilica (c18, 100 μm), inner diameter 1 cm, length 90 cm | | |
| Column temperature | Room temperature | | |
| Mobile phase | methanol:purified water = 65.5:34.5 (v/v) isocratic | methanol:purified water = 67.5:32.5 (v/v) isocratic | methanol:purified water = 70:30 (v/v) isocratic |
| Flow rate | 5.4 ml/min. | 5.4 ml/min. | 5.4 ml/min. |
| Sample injection | docetaxel 0.6 g/methanol 4.8 ml, purified water 1.2 ml | | |
| detector | UV (230 nm) | | |

<3-2> Concentration by Acid
3-2-1. Concentration by Acid (0.5%)

To 120 ml of the docetaxel aliquot of Example <3-1-1>, 0.6 ml (0.5%) of acetic acid was added and the mixture was concentrated under reduced pressure at a temperature of 45° C. The maximum amount of methanol was removed by concentrating under reduced pressure to induce precipitation of docetaxel, and the preipicate was filtered under reduced pressure using a filter paper (Whatman No. 2). The docetaxel precipitate obtained after the filtration under reduced pressure was vacuum-dried at a temperature of 45° C. under reduced pressure of 760 mmHg for 1 day.

The amount of recovered dry solid substance was 0.27 g, purify was 94%, and the yield was 99%.

3-2-2. Concentration by Acid (1%)

To 105 ml of the docetaxel aliquot of Example <3-1-2>, 1.05 ml (1%) of acetic acid was added and the mixture was concentrated under reduced pressure at a temperature of 45° C. The maximum amount of methanol was removed by concentrating under reduced pressure to induce precipitation of docetaxel, and the preipicate was filtered under reduced pressure using a filter paper (Whatman No. 2). The docetaxel precipitate obtained after the filtration under reduced pressure was vacuum-dried at a temperature of 45° C. under reduced pressure of 760 mmHg for 1 day.

The amount of recovered dry solid substance was 0.27 g, purify was 94%, and the yield was 98%.

3-2-3. Concentration by Acid (5%)

To 85 ml of the docetaxel aliquot of Example <3-1-3>, 4.2 ml (5%) of acetic acid was added and the mixture was concentrated under reduced pressure at a temperature of 45° C. The maximum amount of methanol was removed by concentrating under reduced pressure to induce precipitation of docetaxel, and the preipicate was filtered under reduced pressure using a filter paper (Whatman No. 2). The docetaxel precipitate obtained after the filtration under reduced pressure was vacuum-dried at a temperature of 45° C. under reduced pressure of 760 mmHg for 1 day.

The amount of recovered dry solid substance was 0.26 g, purify was 92%, and the yield was 98%.

<3-3> High-Pressure Normal-Phase Chromatography

The dry solid substance obtained in Example <3-2> was completely dissolved in 2 ml of dichloromethane to prepare a sample. Chromatography was conducted using a column filled with silica gel 20 μm under operation conditions as described in the following Table 12. About 40 minutes after the sample injection, an active fraction of docetaxel was aliquoted and concentrated under reduced pressure at a temperature of 45° C. to concentrate the docetaxel aliquot. After the concentration was completed, the concentrate was vacuum-dried at a temperature of 45° C. under reduced pressure of 760 mmHg for 1 day.

The purities and yields of the recovered dry solid substances are described in the following Table 13.

TABLE 12

| Kinds of column | Silica gel 20 μm, inner diameter 2 cm, length 90 cm |
|---|---|
| Column temperature | Room temperature |
| Mobile phase | dichoromethane:methanol = 97.5%:2.5% (v/v); isocratic |
| Flow rate | 15 ml/min. |
| Sample injection | Dry solid substance/dichloromethane 2 ml |
| detector | UV (230 nm) |

TABLE 13

| | Sample | | |
|---|---|---|---|
| | Example 3-2-1 | Example 3-2-2 | Example 3-2-3 |
| Sample injection | docetaxel 0.27 g/ dichloromethane 2 ml | docetaxel 0.27 g/ dichloromethane 2 ml | docetaxel 0.26 g/ dichloromethane 2 ml |
| detector | | UV (230 nm) | |
| Dry solid substance (g) | 0.26 | 0.25 | 0.25 |
| purity (%) | 99.5 | 99.5 | 99.6 |
| Recovery rate (%) | 95 | 95 | 96 |

<3-4> Recrystallization

The docetaxel having purity of 99.8% of Example <3-3> was treated as described in the following Table 14, and stored at a temperature of 4° C. for 12 hours to induce recrystallization. After 12 hours, filtration under reduced pressure was conducted using a filter paper (Whatman No. 42). The docetaxel obtained by the filtration under reduced pressure was vacuum-dried at a temperature of 45° C. under reduced pressure of 760 mmHg for 6 days to obtain anhydrous crystalline docetaxel.

The purities and yields of the recovered dry solid substance are described in the following Table 14.

TABLE 14

| | Experiment group | | |
|---|---|---|---|
| | recrystallization-1 | recrystallization-2 | recrystallization-3 |
| Sample | 0.26 g | 0.25 g | 0.25 g |
| Acetone (ml) | 2.6 | 2.5 | 2.5 |
| Hexane (ml) | 5.98 | 5.75 | 5.75 |
| Dry solid substance (g) | 0.24 | 0.23 | 0.23 |
| Purity (%) | 99.7 | 99.8 | 99.7 |
| Recovery rate (%) | 92 | 93 | 92 |

<3-5> Summarization of the Results of Example 3

Purities and yields according to each process in Example 3 are described in the following Table 15.

TABLE 15

| | Purity of docetaxel (%) | Recovery rate (%) |
|---|---|---|
| Starting material: semi-synthesized docetaxel | 45 | 100 |
| Low-pressure reversed-phase chromatography[methanol:purified water = 65.5:34.5 (v/v)] | 84 | 95 |
| Concentration by acid (0.5%) | 94 | 99 |
| High-pressure normal-phase chromatography | 99.5 | 95 |
| Recrystallization [acetone:hexane = 1:2.3 (v/v)] | 99.7 | 92 |
| Total | 99.7 | 86 |
| Starting material: semi-synthesized docetaxel | 45 | 100 |
| Low-pressure reversed-phase chromatography[methanol:purified water = 67.5:32.5 (v/v)] | 84 | 94 |
| Concentration by acid (1%) | 94 | 98 |
| High-pressure normal-phase chromatography | 99.5 | 95 |
| Recrystallization[acetone:hexane = 1:2.3 (v/v)] | 99.8 | 93 |

TABLE 15-continued

|  | Purity of docetaxel (%) | Recovery rate (%) |
| --- | --- | --- |
| Total | 99.8 | 81 |
| Starting material: semi-synthesized docetaxel | 45 | 100 |
| Low-pressure reversed-phase chromatography[methanol:purified water = 70:30 (v/v)] | 80 | 96 |
| Concentration by acid (5%) | 90 | 98 |
| High-pressure normal-phase chromatography | 99.6 | 96 |
| Recrystallization[acetone:hexane = 1:2.3 (v/v)] | 99.7 | 92 |
| Total | 99.7 | 83 |

Residual solvent contents of Example 3 are described in the following Table 16.

TABLE 16

|  | methanol (ppm) | dichloro-methane (ppm) | acetone (ppm) | hexane (ppm) | Acetic acid (ppm) |
| --- | --- | --- | --- | --- | --- |
| Limit concentration standard (ICH guideline*) | 3,000 | 600 | 5,000 | 290 | 5,000 |
| recrystallization-1 | 29 | 45 | 31 | 65 | 40 |
| recrystallization-2 | 38 | 40 | 40 | 48 | 38 |
| recrystallization-3 | 31 | 37 | 39 | 55 | 22 |

As described above, it can be seen that anhydrous crystalline docetaxel having purity of 99.5% or more may be prepared by sequentially conducting low-pressure reversed-phase chromatography of semi-synthesized docetaxel, concentration by acid, high-pressure normal-phase chromatography, and recrystallization, and that the prepared docetaxel has remarkably lower residual solvent contents than the standard for residual solvents in drugs, implying that it may be a promising source as an anticancer agent.

<Comparative Example 1>

Concentration in Absence of Acid after Primary Purification by Low-pressure Normal-phase Chromatography Followed by Secondary Purification by Low-pressure Reversed-phase Chromatography 70 ml (docetaxel amount 1.0 g, purity 99.4%) of the docetaxel aliquot obtained in Example <1-2> was directly concentrated under reduced pressure at a temperature of 45° C. without adding acid. The maximum amount of methanol was removed by the concentration under reduced pressure to generate docetaxel precipitate, and the precipitate was filtered under reduced pressure using a filter paper (Whatman No. 42). The docetaxel precipitate obtained by the filtration under reduced pressure was vacuum-dried at a temperature of 45° C. under reduced pressure of 760 mmHg for 6 days.

The amount of recovered dry solid substance was 0.94 g, purity was 88%, and yield was 80%.

<Comparative Example 2>

Concentration with 0.01% Acid after Primary Purification by Low-pressure Normal-phase Chromatography Followed by Secondary Purification by Low-Pressure Reversed-phase Chromatography To 70 ml (docetaxel amount 1.0 g, purity 99.4%) of the docetaxel aliquot obtained in Example <1-2>, 0.007 ml (0.01% (v/v) of acetic acid was added, and the mixture was concentrated under reduced pressure at a temperature of 45° C. The maximum amount of methanol was removed by the concentration under reduced pressure to generate docetaxel precipitate, and the precipitate was filtered under reduced pressure using a filter paper (Whatman No. 42). The docetaxel precipitate obtained by the filtration under reduced pressure was vacuum-dried at a temperature of 45° C. under reduced pressure of 760 mmHg for 6 days.

The amount of recovered dry solid substance was 0.90 g, purity was 85%, and yield was 77%.

<Comparative Example 3>

Concentration with 20% Acid after Primary Purification by Low-pressure Normal-phase Chromatography Followed by Secondary Purification by Low-pressure Reversed-phase Chromatography To 70 ml (docetaxel amount 1.0 g, purity 99.4%) of the docetaxel aliquot obtained in Example <1-2>, 14 ml (20% (v/v) of acetic acid was added, and the mixture was concentrated under reduced pressure at a temperature of 45° C. The maximum amount of methanol was removed by the concentration under reduced pressure to generate docetaxel precipitate, and the precipitate was filtered under reduced pressure using a filter paper (Whatman No. 42). The docetaxel precipitate obtained by the filtration under reduced pressure was vacuum-dried at a temperature of 45° C. under reduced pressure of 760 mmHg for 6 days.

The amount of recovered dry solid substance was 0.87 g, purity was 85%, and yield was 72%.

The invention claimed is:

1. A method for preparing anhydrous crystalline docetaxel having purity of 99.5% or more comprising:
   (a) primarily purifying semi-synthesized docetaxel by low-pressure normal-phase chromatography;
   (b) secondarily purifying the primarily purified docetaxel by low-pressure reversed-phase chromatography;
   (c) adding acid in the concentration of 0.05%(v/v) to 10% (v/v) of docetaxel aliquot obtained after the secondary purification of docetaxcel of (b) to concentrate the secondarily purified docetaxel; and
   (d) recrystallizing the concentrated docetaxel of (c).

2. A method for preparing anhydrous crystalline docetaxel having purity of 99.5% or more comprising:
   (a) primarily purifying semi-synthesized docetaxel by low-pressure normal-phase chromatography;
   (b) secondarily purifying the primarily purified docetaxel by high-pressure reversed-phase chromatography;
   (c) adding acid in the concentration of 0.05%(v/v) to 10% (v/v) of docetaxel aliquot obtained after the secondary purification of docetaxcel of (b) to concentrate the secondarily purified docetaxel; and
   (d) recrystallizing the concentrated docetaxel of (c).

3. A method for preparing anhydrous crystalline docetaxel having purity of 99.5% or more comprising:
(a) primarily purifying semi-synthesized docetaxel by low-pressure reversed-phase chromatography;
(b) adding acid in the concentration of 0.05%(v/v) to 10% (v/v) of docetaxel aliquot obtained after the primary purification of docetaxcel of (a) to concentrate the primarily purified docetaxel
(c) secondarily purifying the concentrated docetaxel by high-pressure normal-phase chromatography; and
(d) recrystallizing the secondarily purified docetaxel.

4. The method according to claims 1, wherein in case the low-pressure normal-phase chromatography is performed, a developing solvent selected from the group consisting of C1-2 halogenated alkanes, a C1-6 organic solvent, and a combination thereof is used.

5. The method according to claim 4, wherein the C1-2 halogenated alkanes are at least one selected from the group consisting of dichloromethane and chloroform, and the C1-6 organic solvent is at least one selected from the group consisting of methanol, benzene, acetone, hexane, and ethylacetate.

6. The method according to claims 1, wherein in case the low-pressure reversed-phase chromatography is performed, a developing solvent selected from the group consisting of a C1-3 organic solvent, purified water, and a combination thereof is used.

7. The method according to claim 6, wherein the C1-3 organic solvent is at least one selected from the group consisting of C1-3 alcohol and acetonitrile.

8. The method according to claim 1, wherein the acid is at least one selected from the group consisting of acetic acid, formic acid and trifluoroacetic acid.

9. The method according to claim 1, wherein the recrystallization solvent is at least one selected from the group consisting of acetone and hexane.

10. The method according to claim 9, wherein both acetone and hexane are used as the recrystallization solvent, and, after acetone is introduced so that the concentration of docetaxel becomes 1%(w/v) to 30%(w/v), hexane is introduced in a volume of 1 to 10 times of the amount of acetone introduced.

11. The method according to claim 2, wherein in case the low-pressure normal-phase chromatography is performed, a developing solvent selected from the group consisting of C1-2 halogenated alkanes, a C1-6 organic solvent, and a combination thereof is used.

12. The method according to claim 3, wherein in case the high-pressure normal-pressure chromatography is performed, a developing solvent selected from the group consisting of C1-2 halogenated alkanes, a C1-6 organic solvent, and a combination thereof is used.

13. The method according to claim 11, wherein the C1-2 halogenated alkanes are at least one selected from the group consisting of dichloromethane and chloroform, and the C1-6 organic solvent is at least one selected from the group consisting of methanol, benzene, acetone, hexane, and ethylacetate.

14. The method according to claim 12, wherein the C1-2 halogenated alkanes are at least one selected from the group consisting of dichloromethane and chloroform, and the C1-6 organic solvent is at least one selected from the group consisting of methanol, benzene, acetone, hexane, and ethylacetate.

15. The method according to claim 2, wherein in case the high-pressure reversed chromatography is performed, a developing solvent selected from the group consisting of a C1-3 organic solvent, purified water, and a combination thereof is used.

16. The method according to claim 3, wherein in case the low-pressure reversed-phase chromatography is performed, a developing solvent selected from the group consisting of a C1-3 organic solvent, purified water, and a combination thereof is used.

17. The method according to claim 15, wherein the C1-3 organic solvent is at least one selected from the group consisting of C1-3 alcohol and acetonitrile.

18. The method according to claim 16, wherein the C1-3 organic solvent is at least one selected from the group consisting of C1-3 alcohol and acetonitrile.

19. The method according to claim 2, wherein the acid is at least one selected from the group consisting of acetic acid, formic acid and trifluoroacetic acid.

20. The method according to claim 3, wherein the acid is at least one selected from the group consisting of acetic acid, formic acid and trifluoroacetic acid.

21. The method according to claim 2, wherein the recrystallization solvent is at least one selected from the group consisting of acetone and hexane.

22. The method according to claim 3, wherein the recrystallization solvent is at least one selected from the group consisting of acetone and hexane.

23. The method according to claim 21, wherein both acetone and hexane are used as the recrystallization solvent, and, after acetone is introduced so that the concentration of docetaxel becomes 1%(wlv) to 30%(w/v), hexane is introduced in a volume of 1 to 10 times of the amount of acetone introduced.

24. The method according to claim 22, wherein both acetone and hexane are used as the recrystallization solvent, and, after acetone is introduced so that the concentration of docetaxel becomes 1%(w/v) to 30%(w/v), hexane is introduced in a volume of 1 to 10 times of the amount of acetone introduced.

* * * * *